(12) United States Patent
Béduer et al.

(10) Patent No.: US 11,524,092 B2
(45) Date of Patent: Dec. 13, 2022

(54) PARTICLE SUITABLE FOR THE MANUFACTURE OF AN IMPLANTABLE SOFT TISSUE ENGINEERING MATERIAL

(71) Applicant: École Polytechnique Fédérale de Lausanne (EPFL), Lausanne (CH)

(72) Inventors: Amélie Béduer, Lausanne (CH); Thomas Braschler, Chavannes (CH); Philippe Renaud, Préverenges (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 16/650,555

(22) PCT Filed: Oct. 4, 2018

(86) PCT No.: PCT/CH2018/000041
§ 371 (c)(1),
(2) Date: Mar. 25, 2020

(87) PCT Pub. No.: WO2019/068207
PCT Pub. Date: Apr. 11, 2019

(65) Prior Publication Data
US 2020/0384152 A1 Dec. 10, 2020

(30) Foreign Application Priority Data
Oct. 5, 2017 (WO) ................ PCT/CH2017/000090

(51) Int. Cl.
*A61L 27/20* (2006.01)
*A61F 2/00* (2006.01)
(Continued)

(52) U.S. Cl.
CPC ............ *A61L 27/20* (2013.01); *A61F 2/0059* (2013.01); *A61F 2/12* (2013.01); *A61K 9/141* (2013.01);
(Continued)

(58) Field of Classification Search
CPC ...... A61L 27/20; A61L 24/0036; A61L 27/16; A61L 27/18; A61L 27/24; A61L 27/3633;
(Continued)

(56) References Cited

U.S. PATENT DOCUMENTS

| | | |
|---|---|---|
| 5,629,191 A | 5/1997 | Cahn |
| 7,993,679 B2 | 8/2011 | Ingram et al. |

(Continued)

FOREIGN PATENT DOCUMENTS

WO 2017029633 A1 2/2017

OTHER PUBLICATIONS

Bencherif et al. "Injectable preformed scaffolds with shape-memory properties", PNAS</i>, Nov. 27, 2012, vol. 109, No. 48, pp. 19590-19595. (Year: 2012).*

(Continued)

*Primary Examiner* — Casey S Hagopian
(74) *Attorney, Agent, or Firm* — Pabst Patent Group LLP

(57) ABSTRACT

The particle (1) is suitable for the manufacture of an implantable soft tissue engineering material and comprises: a three-dimensionally warped and branched sheet (2) where (i) the three-dimensionally warped and branched sheet (2) is made from a biocompatible material having a Young's modulus of 1 kPa to 1 GPa; (ii) the three-dimensionally warped and branched sheet (2) has an irregular shape which is encompassed in a virtual three-dimensional envelope (3) having a volume $V_E$; (iii) the three-dimensionally warped and branched sheet (2) has a mean sheet thickness T; iv) the three-dimensionally warped and branched sheet (2) has a volume $V_S$; (v) the particle (1) has a Young's modulus of 100 Pa to 15 kPa; and (vi) the particle (1) further comprises a number of protrusions where the three-dimensionally warped and branched sheet (2) reaches the envelope (3); (vii) the particle (1) has a number of interconnected channel- (Continued)

type conduits (5) defined by the branching of the sheet (2) and/or by voids in the sheet (2); and (viii) where the conduits (5) have (a) a mean diameter $D_C$; and (b) an anisotropicity index of 1.01 to 5.00.

21 Claims, 10 Drawing Sheets

(51) Int. Cl.

| | |
|---|---|
| A61L 27/16 | (2006.01) |
| A61L 27/18 | (2006.01) |
| A61L 27/24 | (2006.01) |
| A61L 27/52 | (2006.01) |
| A61L 27/54 | (2006.01) |
| A61L 27/36 | (2006.01) |
| A61L 27/56 | (2006.01) |
| A61F 2/12 | (2006.01) |
| A61L 24/00 | (2006.01) |
| A61K 9/14 | (2006.01) |

(52) U.S. Cl.
CPC .......... *A61L 24/0036* (2013.01); *A61L 27/16* (2013.01); *A61L 27/18* (2013.01); *A61L 27/24* (2013.01); *A61L 27/3633* (2013.01); *A61L 27/52* (2013.01); *A61L 27/54* (2013.01); *A61F 2240/001* (2013.01); *A61L 27/56* (2013.01); *A61L 2300/00* (2013.01); *A61L 2300/23* (2013.01); *A61L 2400/06* (2013.01); *A61L 2430/04* (2013.01); *A61L 2430/34* (2013.01)

(58) Field of Classification Search
CPC .......... A61L 27/52; A61L 27/54; A61L 27/56; A61L 2300/00; A61L 2300/23; A61L 2400/06; A61L 2430/04; A61L 2430/34; A61F 2/0059; A61F 2/12; A61F 2240/001; A61K 9/141
See application file for complete search history.

(56) References Cited

U.S. PATENT DOCUMENTS

| | | |
|---|---|---|
| 2015/0057368 A1 | 2/2015 | Connelly et al. |
| 2016/0101213 A1* | 4/2016 | Seyedin .............. A61L 27/3817 424/486 |
| 2017/0196818 A1* | 7/2017 | Shin ........................ A61K 35/28 |

OTHER PUBLICATIONS

Wei et al., Chapter 5—Polymeric Biomaterials in Handbook of Biopolymers and Biodegradable Plastics, 2013, pp. 87-107. (Year: 2013).*

Bencherif et al. "Injectable preformed scaffolds with shape-memory properties", PNAS, Nov. 27, 2012, vol. 109, No. 48, pp. 19590-19595 (Year: 2012).*

Definition of "polysaccharide". Oxford English Dictionary. Accessed online on May 21, 2021 at www.oed.com. (Year: 2021).*

Gundersen et al. "Surface Structure and Wetting Characteristics of Collembola Cuticles", PloS ONE, vol. 9, Issue 2, Feb. 2014, pp. 1-11. (Year: 2014).*

International Search Report dated Dec. 17, 2018 filed in PCT/CH2018/000041.

Bencherif, S.A. et al., "Injectable preformed scaffolds with shape-memory properties," Proceedings of the National Academy of Sciences, Nov. 27, 2012, pp. 19590-19595, vol. 109 No. 48, U.S. National Academy of the Sciences, US; Cited in Specification and International Search Report.

Béduer, Amélie et al., A Compressible Scaffold for Minimally Invasive Delivery of Large Intact Neuronal Networks, Advanced Healthcare Materials, Jan. 1, 2015, pp. 301-312, vol. 4 No. 2, Wiley-VCH Verlag GmbH & Co. KGaA, Germany; Cited in Specification and ISR.

Gun'Ko, Vladimir et al., "Cryogels: Morphological, structural and adsportion characterisation", Advances in Colloid and Interface Science, Jan. 1, 2013, pp. 1-46, vol. 187-188, Elsevier B.V., The Netherlands; Cited in ISR.

* cited by examiner

PARTICLE SUITABLE FOR THE MANUFACTURE OF AN IMPLANTABLE SOFT TISSUE ENGINEERING MATERIAL

BACKGROUND OF THE INVENTION

1. Field of the Invention

The invention relates to a particle suitable for the manufacture of an implantable soft tissue engineering material, to an implantable soft tissue engineering material comprising a multitude of particles and method for manufacturing such particles.

2. Description of the Related Art

From U.S. Pat. No. 7,993,679B2 a flowable collagen/glycosaminoglycan material is known which can be used as a wound dressing. This material has no capacity to be expandable.

From U.S. Pat. No. 5,629,191 a method is known for making a mass of general spherical porous matrix particles, which, however, have no capacity to undergo expansion upon uptake of liquid and have spherical shapes with no protrusions.

From the scientific article "Injectable preformed scaffold with shape-memory properties", Bencherif et al., Proceedings of the national academy of sciences, vol. 109, no. 48, Nov. 12, 2012, pages 19590-19595 a process is known in which a polymerizable material is cross-linked using a radical polymerization process starting at a temperature of +4° C. and continued at an unknown temperature. The premixed polymerization mixture is then poured on a pre-cooled mold producing a skinning effect consisting of the partial closing of external pores. The polymerized scaffold material is then used as such for injection into a patient, i.e. with no further fractioning of the scaffold obtained.

Other prior art manufacturing processes start from pre-existing tissues as a raw material for producing particulate implantable soft tissue materials. The disadvantage of such methods lays in the fact that hardness and elasticity of the particles, which are essential for the intended volume reconstruction process, cannot be adjusted.

Other known processes start from frozen material, which gives less elastic and less porous particles.

A) General Definitions

Soft Tissue Engineering Material

A biocompatible material for use in reconstruction, repair, enhancement, augmentation or substitution of soft tissues. In the context of this invention, a material obtained by combination of the branched-sheet 3D particles with a physiologically acceptable fluid (physiological saline, phosphate buffered saline, blood plasma, living aspirates such as lipoaspirate).

Dry Mass Concentration

The dry mass concentration of the soft tissue engineering material can be determined by standard techniques known in the art, i.e. washing of the particles to remove salts followed by drying to constant weight, and relating the dry weight found in this way to the volume of the soft tissue engineering material.

B) Definitions Concerning the Reference Conditions

Reference Liquid and Reference Measurement Condition

The geometric and mechanical properties of sheet material, particles, and soft tissue engineering material all depend on the suspension liquid. It is therefore necessary to specify the reference liquid in which such values are measured. For the present invention, this liquid is phosphate buffered saline, with the following concentrations: potassium chloride (KCl) 2.6 mM, potassium phosphate monobasic ($KH_2PO_4$): 1.5 mM, sodium chloride (NaCl) 138 mM, sodium phosphate dibasic ($Na_2HPO_4$): 8.1 mM in deionized water. Knowing these concentrations, a person skilled in the art will be able to prepare the reference liquid. The measurement of geometrical and mechanical properties of samples should be carried out with samples immerged for at least 24 h with at least a 100× excess of reference liquid relative to the sample volume prior to the measurement and immerged in the reference liquid during the measurement. The reference temperature is room temperature (25° C.).

C) Geometric Definitions

Particle Size

The size of a particle is defined by the volume of its convex hull. The convex hull is a well-known mathematical concept; it comprises all the material points making up the particle, and also all possible straight-line connections between these material points. The convex hull can be determined by confocal imaging of freely suspended, isolated particles in the reference liquid. A non-exclusive example of determination of the size of a particle in accordance with the invention involves the following steps, known to a person skilled in the art:

1) Confocal microscopy according to techniques known in the art is used to acquire an image of an isolated particle freely suspended in the reference liquid. Confocal imaging can typically be done based on autofluorescence of the sheet material or fluorescence from dyes displaying affinity or on the contrary being excluded from the sheet material. 2) The confocal images acquired are stored electronically as stacks of images, each image corresponding to a confocal plane. The pixels making up these images are also referred to as voxels since they represent the fluorescence information from a confocal volume of a certain depth.

3) Each voxel is then either assigned to the sheet material or the void space (based on thresholding between two very distinct populations of intensities).

4) Using this binarized representation, the convex hull constructed using available software. For the particles at hand, the convex hull defines a mostly polyhedral 3D volume that contains all the voxels of the branched sheet but also the pore space interior to the particle.

5) Finally, the total particle volume can be calculated by the number of voxels identified as belonging to the convex hull times the volume associated with each voxel.

Equivalent Particle Diameter

The equivalent particle diameter is the diameter of sphere that has the same volume as the particle's convex (the "particle size"). To be specific, if the volume of the particle is V, then the equivalent diameter is given $d=(6*V/pi)^{(1/3)}$, where $pi=3.1419\ldots$.

Envelope of a Particle

The envelope of a particle is defined by the surface of its convex hull. As a non-exclusive example, a digital representation of the convex hull of a given particle can be obtained by the sequence outlined for the particle size above (i.e. confocal images of freely suspended particles in the reference fluid are acquired, stored, and analyzed as described for the size of the particle to define its convex hull). The envelope of the particle is defined by the voxels of the convex hull that have at least one direct neighbor (sharing a face or corner) that does not belong to the convex hull.

Protrusions of the Particle

The protrusions with the particle surface are defined as the parts of the sheet that reach the envelope of the particle as defined above. As a non-exclusive example, a digital representation of the protrusions can be defined from the approach described for the envelope of the particle. Indeed, once the digital representation of the envelope is defined, the location of the waU protrusions is found by taking the intersection of the voxels representing the branched sheet and the voxels representing the particle envelope.

Protrusion Depth

The protrusion depth is defined by the length of a normal vector from a point of the particle envelope to the closest intersection point with a sheet of the particle. If the point of interest of the particle envelop belongs itself to a sheet, the associated protrusion depth is zero. If the normal vector has no intersection with a sheet, the distance between the two intersection points of the normal vector with the envelope is taken instead.

Maximal Protrusion Depth

The maximal protrusion depth is largest observed protrusion depth for a given particle.

Relative Maximum Protrusion Depth

The relative maximum protrusion depth is defined as the maximum protrusion depth divided by the equivalent particle diameter. If larger than 1, a value of 1 is recorded.

Contact Area of the Protrusions

The contact area of the protrusions is the area where the distance from the envelope to the nearest sheet is less than the average sheet thickness TC.

Conduits

The conduits are the voids inside the particles. In the soft tissue engineering material, they can be filled with a physiologically acceptable fluid.

Conduit Diameter Dc

The conduit diameter Dc is defined as the mean Feret diameter of the conduits as individual void areas on a section of the particle. To determine the conduit diameter Dc, 2D cross section images of particles freely suspended in reference liquid may be obtained, for instance by confocal imaging. On such sections, the conduits are identified as the visible distinct voids; for conduits reaching the particle exterior on the section of interest, the boundary of the convex hull of the particle as visible on the 2D section is used to complete delimitation of the void by the sheet material. For each of the voids identified, the Feret diameter, known to a person skilled in the art, is measured in all possible orientations (in practice, a few hundred), and the average taken for each void. To obtain the average conduit diameter, the average of these averages is taken, ideally for several sections of several particles.

Thickness of the Sheet T

The average thickness of the sheet T is defined as the mean thickness of sheet material encountered when randomly slicing the particle. To determine the average thickness of the sheet T, 2D cross section images of particles freely suspended in reference liquid may be obtained, for instance by confocal imaging. On such images, pixels are either attributed to the sheet material or the pore fraction, typically based on intensity thresholding. To determine the sheet thickness, random straight lines are drawn across the particle (random orientation, random localization). For each such line, transitions from void to sheet and back are noted, each such transition from void to sheet and back representing a sheet intersection. The local thickness of the sheet for such a sheet intersection is determined from the number of pixels belonging to the walls and the known size of the pixels. The average thickness of the sheet T is obtained by averaging over all the sheet intersection, ideally from hundreds of lines per particle and also a statistically relevant number of particles.

Relative Sheet Thickness

The relative sheet thickness is the ratio of the sheet thickness to conduit diameter: $T_{relative}=T/(D_C+T)$. For particles with low relative sheet thickness $T_{relative}$ (i.e. $T_{relative}<0.1$) one expects the total sheet volume fraction to be proportional to $T_{relative}$, with a proportionality constant near unity.

Conduit Diameter, Sheet Thickness and Relative Sheet Thickness in the Soft Tissue Engineering Material Conduit diameter, sheet thickness and relative sheet thickness are not only defined for the isolated particles, but also for the soft tissue engineering material. In this case, they are understood to depend on the amount and nature of the fluid added to obtain the soft tissue engineering material. They can be measured by the same methodology as the one exposed for the particles, i.e. by acquisition of planar images for instance by confocal imaging, following by the image analysis techniques defined above. In the case of the soft tissue engineering material, one should be aware that the conduits detected as voids will generally be conduits within particles, but also conduits formed between neighboring particles; except for if particular precautions such as labeling of different particles with different dyes are taken, it is not generally possible to distinguish between the two. Likewise, some of the sheet intersections in the procedure for determining sheet thickness will be formed by touching sheets from neighboring particles, without this being necessarily evident in image analysis.

Branched Sheet Morphology

The branched sheet morphology applies to the particles. Porous materials in general are classified either as "open" or "closed" foams (Cellular Solids: Structure and Properties, Gibson and Ashby). In the terminology of foam science, closed foams have "cells" (pores, voids) where the faces shared with neighboring "cells" are solid membranes (Cellular Solids: Structure and Properties, Gibson and Ashby); these closed foams entrap the pore fluid, which cannot easily escape through the solid membranes delimiting the "cells". Classical open foams have no membranes between neighboring cells, but only struts along the edges where three or more cells meet (Cellular Solids: Structure and Properties, Gibson and Ashby). Such open foams naturally have a fully interconnected pore space, and a fibrous network of solid material. The branched sheet morphology can be seen as a special structure that functionally combines aspects of open and closed foams. In a perfect branched sheet morphology, each "cell" can be understood to have both open and closed faces. The open faces provide connections to neighboring "cells", while the closed faces make up the bulk of the branched sheet. The open faces are organized in such a way to allow connectivity to the particle exterior for the vast majority of the foam cells, and hence to provide pore interconnectivity. The closed faces together provide the branched and warped 3D-sheet morphology. Typically, each "cell" has at least two open and two closed faces, where an open face can also be a connection to the particle exterior.

Anisotropicity Index

The anisotropy index is the ratio between the longest Feret diameter to the smallest Feret diameter of a body or void. In the context of this invention the anisotropicity index refers to the conduits, i.e. the ratio between longest and smallest Feret diameter for each conduit, as individualized as a distinct void in 2D cross-sectional images (see conduit diameter Dc). The global anisotropy index is the average of the anisotropy indexes associated with the individual conduits, as identified as individual voids on 2D cross-sections.

D) Definitions Concerning Mechanical Properties

Young's Modulus

The Young's modulus of a given material is the ratio between stress (force per area) and strain (deformation relative to the original length) as measured in uniaxial compression, typically for small strains (10% compression or less). For the present invention, Young's moduli are defined at three different scales: the Young's modulus of the material from which the branched sheets are made; the Young's modulus of the resulting particles; and the Young's modulus of the assembled soft tissue engineering material.

Young's Modulus of the Sheet Material

The Young's modulus of the sheet material is the Young's modulus as measured on a pure, non-porous sample of the sheet material, in the reference liquid. In some embodiments, the sheet material can not only be synthesized as porous, branched sheet particles, but also as sufficiently large bulk material. In this case, the most precise method of evaluation of the Young's modulus of the sheet material is by direct mechanical testing of a bulk sample of the sheet material (under reference conditions). In other embodiments, it is difficult to produce the sheet material in homogeneous bulk quantities; in this case, the Young's modulus of the sheet material can still be evaluated by microindentation techniques, directly on structured materials, as for instance described in Welzel et al., Adv Healthc Mater 2014, or Beduer at al., Advanced Healthcare materials 2015. 4(2): p. 301-12, using the reference conditions given above.

Young's Modulus of the Particles

As there is no technique known to directly assess the Young's modulus of the irregular, porous particles of the present invention, macroscopic samples with regular geometries (typically cylinders of a few mm heights and 1 or 2 cm diameter), but with identical pore structure and sheet material are produced for mechanical testing. It is then possible to use standard mechanical testing equipment to impose the desired uniaxial deformation, and to measure the associated force to determine strain (deformation relative to original sample height) and stress (force per cross-sectional area) to calculate the Young's modulus of the particles under reference conditions. As it will be known to a person skilled in the art, the mechanical testing of porous samples heavily depends on the boundary conditions for the pore fluid. Under the reference conditions, the sample is immersed in reference fluid, and is therefore under so-called drained conditions. Nevertheless, to avoid undue influence of the drainage of the pore fluid on the measured Young's modulus, it is important to ensure that the fluidic drainage resistance of the sample becomes negligible with respect to the solid's response. In practice, it will be known to a person skilled in the art that the primary variables to control in this respect are sample geometry and compression rate, and that suitable compression conditions can be found for instance through minimization of hysteresis or validation by stress relaxation tests.

Young's Modulus of the Soft Tissue Engineering Material

A third Young's modulus applies to the soft tissue engineering material. The soft tissue engineering material consists of a given amount of particles (specified for instance relative to the original amount fabricated or absolutely in terms of dry mass present), and a specified amount of reference fluid. For a wide range of fluid volume to particle mass, this mix forms a paste with a non-zero yield stress and strain (measurable through rheometry), meaning that the paste behaves like a solid for sufficiently small deformations. For such small deformations, the Young's modulus can be measured by uniaxial compression. The Young's modulus naturally depends on the ratio of particles to fluid, the composition and geometry of the particles, as well as the composition of the fluid.

In practice, it should be noted that soft tissue engineering material cannot simply be immerged into the reference fluid, undue dispersal of the particles would result. Instead, the drainage of reference pore fluid during compression has to be carried out through a porous membrane, with a pore size such that the reference fluid easily passes, but the particles are retained in the compression area. A person skilled in the art will easily be able to adapt existing setups to this purpose or identify a suitable commercial apparatus.

Deployment Pressure

The deployment pressure is the pressure with which the soft tissue engineering material of this invention expands, and therefore attracts liquid. Like the Young's modulus of the soft tissue engineering material, the deployment pressure depends on the exact nature of the particles suspended, the exact composition of the fluid used for its measurement, and the ratio of particles to fluid. The deployment pressure of the soft tissue engineering material can be measured by contacting the soft tissue engineering material with a mesh or membrane freely permeable to the reference fluid, but not the particles of the soft tissue engineering material. The deployment pressure is then the difference between the pressure recorded in the soft tissue engineering material and the pressure in pure reference fluid in equilibrium with the soft tissue engineering material. A possible readout technique is observation of hydrostatic height differences in a U-tube configuration with the separation membrane between soft tissue engineering material and the pure reference fluid; another possibility is the use of pressure gauges, one where only the reference fluid has access, the other exposed to the soft tissue engineering material.

Maximal Elongation of the Sheet Material

The maximal elongation of the sheet material is the maximum relative deformation of the sheet material compatible with essentially purely elastic deformation in the reference liquid: beyond this maximal elongation, the sheet material fails by either onset of plastic deformation or brittle fracture.

Swelling Value of a Material

The swelling value is defined as the relative weight change of a material from dry to humid state. This parameter is a ration, namely (Humid weight−Dry weight)/Dry weight. The measurement of the swelling value is usually performed in physiological saline 0.9% NaCl.

BRIEF SUMMARY OF THE INVENTION

It is an object of the invention to provide a particle suitable for the manufacture of an of implantable soft tissue engineering material with the capability of the particles to increase the size of its conduits by fluid uptake and therefore to increase the volume of the particles up to a predefinable and controllable volume.

This is achieved thanks to the particular properties of the branched sheets composing the particle.

The invention solves the posed problem with a particle as disclosed and claimed herein and with an implantable soft tissue engineering material as disclosed and claimed herein.

The advantage(s) of the particles according to the invention and of the implantable soft tissue engineering material comprising such particles is to be seen in the ability of the particles to absorb water or aqueous solutions, like body fluids, thereby causing the three-dimensionally warped and branched sheet to deploy so that its envelope will occupy a larger volume. This volume is predefined by the conduits volume.

Compared to other materials the particles according to the invention have shown the unique property that they are capable of deploying back gently, yet rapidly under in-vivo conditions. The reason for this is to be seen in the deployment pressure required for partial swelling that matches the in vivo physiological deployment pressure. For example, too soft porous materials flow and cannot sustain a three-dimensional volume. Since these known materials are too soft its pores (or conduits) are prevented to actively deploy. On the other hand, too hard materials provide a foreign body not matching the mechanical properties of the soft target tissues and are creating a local mismatch of Young's modulus, at the origin of a local inflammatory reaction and possibly fibrosis.

The capacity of deployment of the branched sheet of the particle according to the invention combined with the interconnected porosity in the form of channel-like conduits enables a better bio-integration, i.e. ingrowth of tissues and vessels into the particle compared to state of the art particle without the capability of deployment.

The injectable material allows the filling of tissue defects of small and medium size and even defects larger than 50 cm³.

The protrusions of the particles—which produce an unexpected zip-fastener effect—are an essential feature of the invention. This feature enables cohesivity of the engineering material implanted into the patient. The protrusions are a key feature enabling cohesion between the particles and avoid migration/permanent deformation of the engineering material after its injection into the patient.

A further essential feature of the invention is the degree of anisotropicity of the conduits enabling the volume of the engineering material to be maintained.

It has been found that if the conduits are too anisotropic, the sheets will collapse and stick to each other, leading to spreading of the implanted engineering material and preventing creation of a stable three-dimensional volume.

The deployment of the branched sheets of the particles enables a better and rapid ingrowth of cells, tissues, blood vessels, lymph and extracellular matrices and more stability of the shape and volume of the implanted engineering material.

The zipper-effect of the protrusions enables to maintain the injected shape by avoiding migration of the particles.

Thanks to the combination of the above mentioned features and to the active deployment, the engineering material is able to enter into a frictional relationship with the surrounding tissues enabling the engineering material to stay in place (anchoring).

If the implanted material is too hard, this anchoring effect is replaced by a cutting effect and the tissue is damaged. If the material is too soft, the material is not anchoring and slides over the tissues.

Deployment at low pressures enables the gentle aspiration of tissues or cell suspensions for co-grafting applications, for example mixing of the engineering material with adipose tissues and injection of the mixture to create a living volume.

The low deployment pressure results from particle design. The application imposes the Young's modulus of the particles, but depending on the particle structure, the deployment pressure can vary. To obtain a low deployment pressure for a given Young's modulus, it is essential that compression of the particles can occur as much as possible by evacuation of pore fluid, and not by compression of the incompressible pore fluid or nearly incompressible sheet material itself, as this necessitates greater isotropic pressure. For this, the branched sheet morphology is key: the pore fluid can easily be evacuated through interconnectivity, whereas the closed faces provide mechanical solidity, allowing to keep the sheet volume fraction low and avoiding sheet-to-sheet contact and compression. This combination gives the desired low deployment pressure for the desired Young's moduli.

In a special embodiment of the invention the volume $V_E$ of the envelope is larger than $5 \cdot 10^{-4}$ mm³, preferably larger than $4 \cdot 10^{-3}$ mm³ and most preferably larger than 0.03 mm³ The volume $V_E$ of the envelope is purposefully smaller than $4 \cdot 10^3$ mm³, preferably smaller than 260 mm³, and most preferably smaller than 30 mm³.

The thickness T of the sheet 2 is purposefully larger than 1 μm, preferably larger than 5 μm, The thickness T is purposefully smaller than 1000 μm, preferably smaller than 100 μm, and most preferably smaller than 20 μm. Surprisingly it has been found that a sheet thickness in that range allows obtaining a material which is transparent when imaged with ultrasounds imaging devices (such as the ones used in patients.

The total surface of the sheet 2 is purposefully larger than $8 \cdot 10^{-4}$ mm², preferably larger than $1 \cdot 10^{-2}$ mm², and most preferably larger than $10^{-1}$ mm². The total surface of the sheet 2 is purposefully smaller than 50 000 mm², preferably smaller than 10 000 mm².

The total volume $V_s$ of the sheet 2 is purposefully larger than $8 \cdot 10^{-7}$ mm³, preferably larger than $5 \cdot 10^{-6}$ mm³, and most preferably larger than $5 \cdot 10^{-4}$ mm³. The total volume $V_s$ of the sheet 2 is purposefully smaller than 50 000 mm³, preferably smaller than 5 000 mm³, and most preferably smaller than 200 mm³.

In a special embodiment the anisotropicity index of the conduits 5 is larger than 1.05, preferably larger 1.10. The anisotropicity index is purposefully smaller than 10.0, preferably smaller than 5.0 and most preferably smaller than 3.0.

The material for the sheet can be chosen from non-fouling substances poly-ethyleneglycol (PEG), poly-acrylamide, poly-(Hydroxyethyl)methacrylate, preferably from polysaccharides such as cellulose, methylcellulose, carboxymethylcellulose, agarose, polysucrose or dextran.

The sheet may also comprise a material chosen from the following group: carbohydrates, hydrogels, collagens, gelatins, chitosan, peptides or extracellular matrices. These materials confer biocompatibility and biodegradability.

The carbohydrate can be
(i) a polysaccharide, preferably a negatively charged polysaccharide;
(ii) an alginate;
(iii) hyaluronic acid; or
(iv) a carboxymethyicelluose.

These materials confer elasticity to the particle enabling a reversible compression capability and a reversible fluid intake capability The sheet may also comprise a synthetic polymer, preferably chosen from the following groups
(i) silicones;
(ii) polyurethanes;
(iii) polyolefins;
(iv) acrylates, preferably poly-acrylamide or poly-acrylic acid; poly-(Hydroxyethyl)-methacrylate and copolymers thereof;
(v) polyesters;
(vi) polyamides; or
(vii) polyimides.

The material of the sheet 2 has preferably a maximal elongation of VS/VE or more. This confers a reversible fluid intake capability to the particle.

The material of the sheet 2 has preferably a maximal elongation of $3T/D_C$ or more.

The material of the sheet 2 has purposefully a molecular weight in the range of 50 Da-10 M Da.

In a further embodiment the ratio of $D^C/T$ is larger than 1.0, preferably larger than 2. Purposefully the ratio of $D_C/T$ is larger than 5, preferably larger than 7. The ratio of $D_C/T$ may be smaller than 500, preferably smaller than 100. Purposefully the ratio of $D_C/T$ is smaller than 50, preferably smaller than 30. The ratio of $D_C/T$ may be smaller than 29, preferably smaller than 15. The specific choice of the ratio of $D_C/T$ combined with the choice of material enables the reversible compressibility of the particle and obtaining suitable particle Young moduli.

In a further embodiment the mean diameter $D_C$ of the conduits is larger than 1 micrometer, preferably larger than 14 micrometer. Purposefully the mean diameter $D_C$ of the conduits is larger than 20 micrometers, preferably larger than 50 micrometers. The minimum dimensions for the conduits enable cellular and vascular ingrowth into the particle.

In a further embodiment the mean diameter $D_C$ of the conduits is smaller than 10 mm, preferably smaller than 4 mm. The mean diameter $D_C$ of the conduits may by smaller than 2 mm, preferably smaller than 1 mm.

Purposefully the mean diameter $D_C$ of the conduits is smaller than 600 micrometer preferably smaller than 300 micrometers. The maximum dimension for the conduits enables a mechanical stability of the scaffold and tight contacts between the scaffold and the tissues. If the value for $D_C$ is too high, the cellularization and vascularization is not as high as if $D_C$ is optimal.

It was surprisingly found that the choice of these parameters allows obtaining a material which matches the speckled appearance of native tissue when imaged with ultrasound imaging devices (such as the ones used in patients.

In a further embodiment the protrusions 4 have a mean relative maximum protrusion depth in the range between 0.05 and 1.0, preferentially between 0.15 and 0.8.

The shape of the three-dimensionally warped and branched sheet 2 is purposefully flexible and in particular it is preferably reversibly expandable upon absorption or removal of a liquid by the biocompatible material. Liquids suitable for absorption are water, aqueous solutions, blood or other body fluids.

In a further embodiment the Young's modulus of the biocompatible material of the sheet 2 is at least 200 Pa, preferably at least 1'000 Pa. Purposefully the Young's modulus of the biocompatible material of the sheet 2 is smaller than 500 kPa, preferably smaller than 50 kPa. The material constituting the sheets should have a Young's modulus high enough to avoid compression of the particle at pressures that can be found in the body (fluid pressure of the interstitial fluid). If the material is too "soft", it has become apparent that the sheets collapse one against to each-other and they are not able to expand back to obtain a certain "memory shape" effect observed with stiffer sheets In a further embodiment the mean diameter $D_P$ of the particle is larger than 2 micrometers, preferably larger than 10 micrometers. This feature enables the particle to create a cohesive implant. If particles are too small, there is the risk of migration of the particle in lymph or blood vessels, or phagocytosis by macrophages for example.

The mean diameter $D_P$ of the particle is purposefully smaller than 5 mm, preferably smaller than 2 mm. This limitation of the particle dimension enables at the same time structurability and shapeability of a paste created by a plurality of particles and a cohesivity of the paste.

In a further embodiment the particle comprises at least 5 conduits, preferably at least 10 conduits. A small number of conduits in the particle leads to mechanical properties which are less optimal and the particle will have more chances to collapse.

In a further embodiment the ratio between the mean diameter of the conduit and the mean diameter of the particle $D_C/D_P$ is larger than 1.5, preferably larger than 2.0. Surprisingly it has been found that an optimal $D_C/D_P$ ratio avoids reduced porosity which would reduce also the tissue ingrowth capability. The optimal ratio also leads to a favorable the biodegradation time. Purposefully the ratio between the mean diameter of the conduit and the mean diameter of the particle $D_C/D_P$ is smaller than 20, preferably smaller than 10.

In a further embodiment the contact angle between water and the biocompatible material of the sheet 2 is in the range of 0° to 90°, preferably in the range of 0°-60°. This feature allows an optimal liquid intake in the conduits of the particle.

Preferably the sheet 2 is reversibly compressible.

In a further embodiment the particle is hydrated and preferably comprises at least 0.05 weight-% of the biocompatible material based on the total weight of the hydrated particle. Purposefully the hydrated particle comprises at least 0.1 weight-%, preferably at least 0.5 weight-% of the biocompatible material.

Purposefully the particle is hydrated and comprises at most 15 weight-% of the biocompatible material based on the total weight of the hydrated particle. The hydrated particle may comprise at most 5 weight-%, preferably at most 3 weight-% of the biocompatible material.

The particle according to the invention may comprise several three-dimensionally warped and branched sheets 2.

The invention therefore is also directed to a composition comprising:
a) a multitude of particles according to the invention; and
b) a physiologically acceptable fluid.

The amount of fluid may be such that the particles are only partially hydrated. This has the advantage that the particles of the composition retain still the ability to deploy by up-take of body fluids after injection into the body of the patient.

The invention is further directed to an implantable soft tissue engineering material comprising a multitude of particles according to the invention, preferably in form of a malleable paste. The multitude of particles may be admixed with one or more substances to form a malleable paste, wherein the one or more substances are selected from the group consisting of water, aqueous solution, blood, serum, pharmaceutically active agents, lidocaine, adrenaline, cell suspensions, oxygenating particles suspensions, biological tissues, stem cells, virus, bacteria, fungi, transfecting agents, antibodies, genetically modified cells, cell adhesive moieties, extracellular matrices, co-cultures of cells, growth factors, platelet rich plasma, cell differentiation factors, lipids, LGL, and high-density lipoprotein (HDL). The multitude of particles may be admixed with water or an aqueous solution or blood to form a malleable paste. The multitude of particles may also be admixed to adipose tissue. This has the advantage that the mixing of the paste with adipose tissues allows creating a new volume of adipose tissues.

The implantable soft tissue engineering material according to the invention is purposefully reversibly compressible after injection into a patient by uptaking liquid from the surrounding tissues. The uptake of liquid occurs up to a fixed predefined amount corresponding to the full expansion state of the particles, i.e. until the conduits are filled with liquid. Once the conduits are full, the expansion cannot go further. In vivo, there is then an equilibrium between the particles pressure and the pressure of the in vivo interstitial pressure. At this stage the material is not deformable anymore guaranteeing that the volume created for the patient cannot be deformed anymore.

The implantable soft tissue engineering material according to the invention purposefully exhibits a non-linear compression behavior and a Young's modulus comprised between 100 Pa and 15 kPa.

The implantable soft tissue engineering material according to the invention may be used as a shapeable tissue or organ body implant. The implantable soft tissue engineering material according to the invention may also be used for treating tissue defects, in particular tissue defects caused by severe trauma or cancer ablation. I may also be used for breast reconstruction and for lipofilling. Further the material may be used for aesthetic restorations in the face and the body.

The invention is further directed to a method for manufacturing particles according to the invention comprising the following steps:
  a) pre-cooling a polymerizable biocompatible material in an aqueous solution at a temperature below 10° C.;
  b) cross-linking the pre-cooled mixture at a temperature below 0° C., preferably below minus 1° C.; and
  c) fractioning the cross-linked biocompatible material obtained.

The cross-linking according to step b) may purposefully be performed at a pH-value of minimum 5.0, preferably minimum 5.5.

The cross-linking according to step b) may purposefully be performed at a pH-value of maximum 8.5, preferably maximum 7.5. The cross-linking according to step b) may be performed at a pH-value of maximum 6.9, preferably maximum 6.5.

The cross-linking process in step b) should not be one based on a radical polymerization since it has been found that radical polymerization can pose a hazard problem because of incorporation of initiator and possible depolymerization during sterilization in vitro.

The cross-linker used in step b) may be adipic dihydrazide.

In a special embodiment the cooling process in step b) consists of two sub-steps:
  (i) a first sub-step to a temperature in the range of 0° C. to −15° C., preferably in the range of −2° C. to −12° C., followed by a hold time for temperature equilibrium; and
  (ii) a second sub-step to a temperature in the range of −80° C. to −2° C.

The polymerizable biocompatible material has preferably a molecular weight of 50 Da-10 MDa.

A BRIEF DESCRIPTION OF THE DRAWINGS

A special embodiment of the invention will be described in the following by way of example and with reference to the accompanying drawings in which.

DETAILED DESCRIPTION OF THE INVENTION

Figure 1:
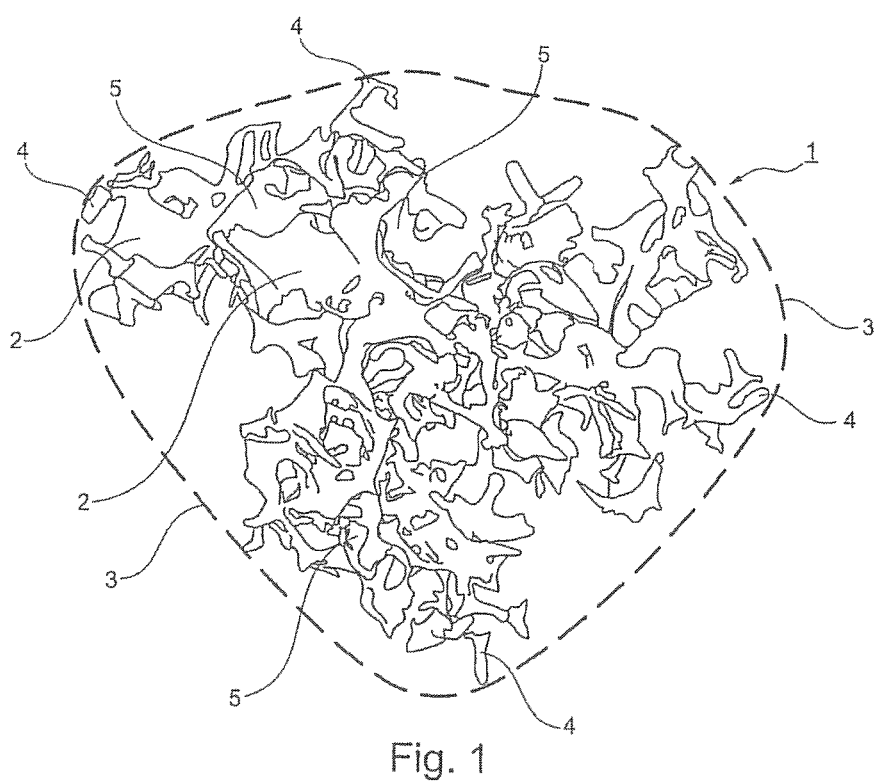
FIG. 1 illustrates a three-dimensional view of an embodiment of the particle according to the invention and its virtual envelope.
Figure 2:
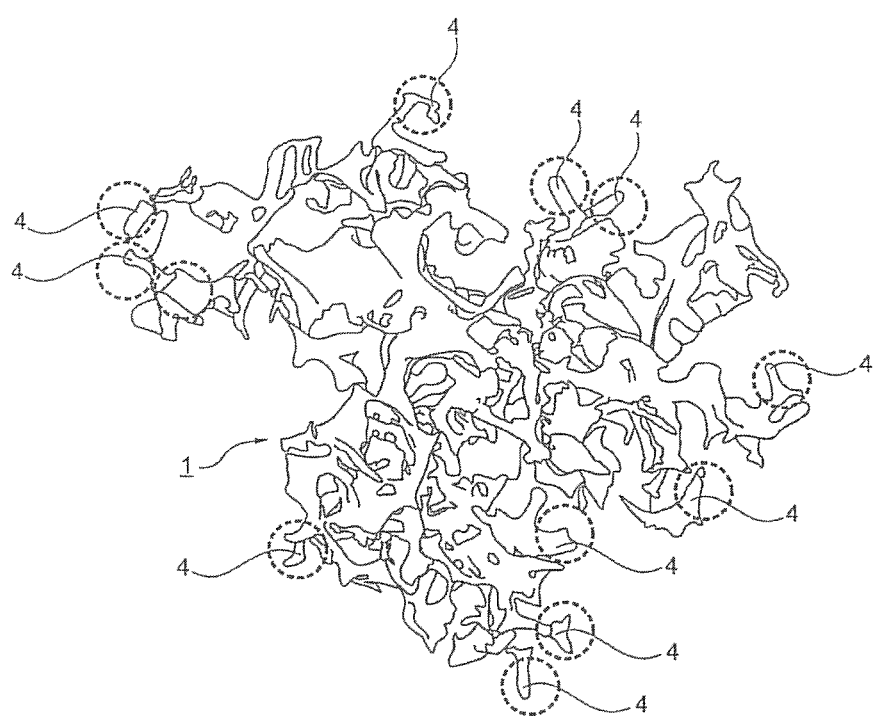
FIG. 2 shows the same view as FIG. 1 highlighting the protrusions at the periphery of the particle by means of broken-line circles.
Figure 3:
FIG. 3 shows the same view as FIG. 1 in which the thickness T of the sheet at various locations is indicated by arrows.
Figure 4:
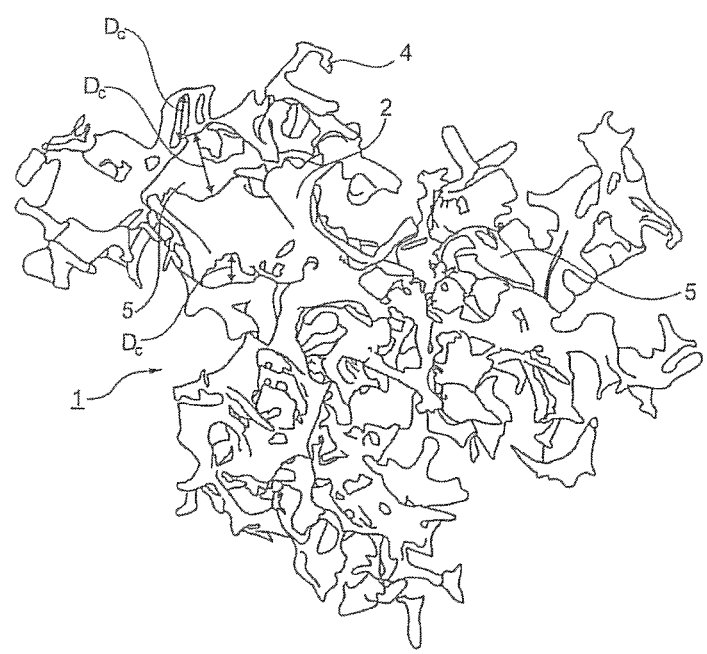
FIG. 4 shows the same view as FIG. 1 in which the thickness diameter DC of some of the conduits is indicated by arrows.
Figure 5:
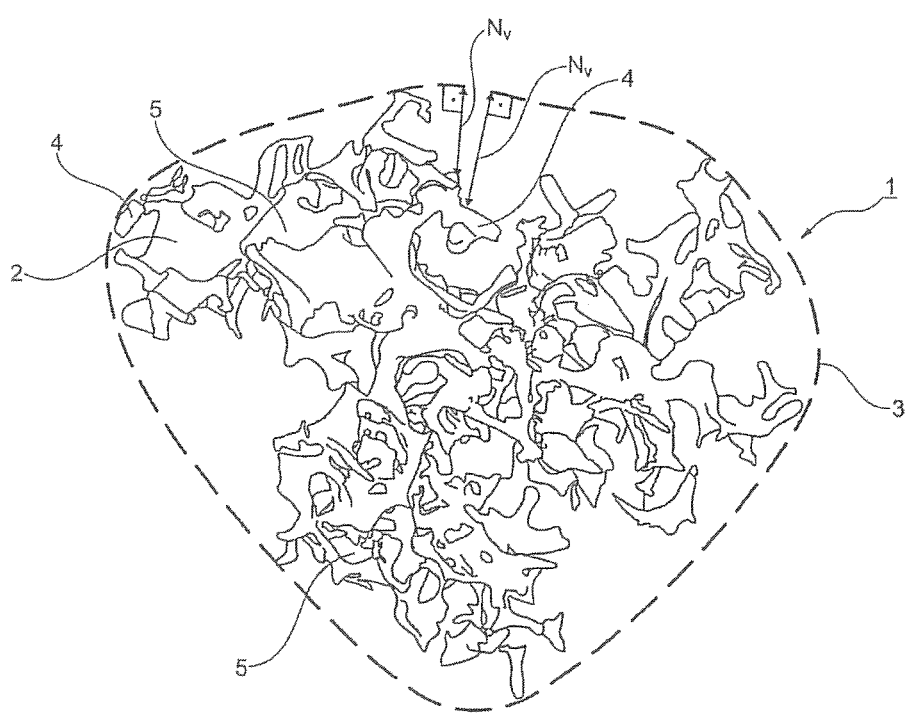
FIG. 5 shows the same view as FIG. 1 in which the protrusion depth is indicated by the length of a normal vector Nv from a point of the particle envelope to the closest intersection point with a sheet of the particle.

The following examples clarify the invention further in more detail.

A) Manufacture of the Particles

Example 1

Carboxymethyl-cellulose (with a MW of 700 kDa) was dissolved in deionized water to the concentration of 2%, and crosslinking initiated after precooling to 4° C. by means of addition of adipic acid dihydrazide AAD (0.07%) and a small excess of the carbodiimide EDC (0.4%) and buffered to a pH-value of 5.5. by means of an excess of 2-(N-morpholino)ethanesulfonic acid (MES) buffer (50 mM).

The reaction mixture was placed at −20° C. in a mold. After 1 day, the scaffolds were thawed and washed in de-ionized water (DI).

The next step consisted in fractioning the scaffold. For this, a bulk scaffold or a bulk scaffold piece was placed in a plastic bag and compressed and sheared manually to create the particles according to the invention. In another embodiment, the bulk scaffold was extruded through a thin tubular element by applying a known pressure to obtain a fragmented material.

The particle size was controlled by the pressure applied on the piston of the syringe and by the size of the extruding cannula. Typically, a pressure of 15 bars and a cannula of 14 G was used.

Example 2a

The same procedure as in example 1 was followed but prior to freezing, the reaction mixture was distributed into a silicone mold using a pipette of 10 mL. The silicone mold contained microstructured star-shaped cavities measuring 100 micrometers in diameter and 20 micrometers in depth. The silicone mold was covered with a flat polypropylene counterpart, squeezing excess liquid from the mold. The assembly was then placed into a freezer at −20° C.

Alternative Methods for the Manufacture of Particles:

Particles were manufactured by placing the scaffolds into a mixer and mixing them.

Particles were manufactured by ink-jet printing, 3D printing, and additive manufacturing.

Particles were manufactured by mixing the reaction mixture with a photosensitizer (typically acrylamide monomer and N,N'methylenebis(acrylamide), freezing at −20° C. and photopolymerizing using a UV lamp or a visible lamp.

Particles were manufactured by grinding a preliminary manufactured scaffold during at least 30 s, for example using a mixing robot (for example Kenwood Major Titanium KMM060).

Particles were manufactured by cutting and/or slicing a preliminary manufactured scaffold using cutting blades, possibly organized in networks.

It is important to note that a classical emulsion polymerization method would give nearly perfectly round particles and therefore would not lead to the desired structure of the particles according to the invention with significant protrusions.

Example 2b

A solution of 5% of hyaluronic acid monomers with a molecular weight of 90 kDa, MES buffer pH6, adipic acid dihydrazide (2 mg/mL) was mixed with EDC (4 mg/mL) and poured onto a consolidated paraffin microspheres scaffold. The paraffin beads were prepared according to "Microspheres leaching for scaffold porosity control", Draghi et al, Journal of Material sciences: Materials in medicine, 16 (2005) 1993-1997. The mixture was incubated at room temperature during 24 hours after which the paraffin beads were dissolved by an excess of hexane. The obtained scaffold was then rinsed with isopropanol, and a mix of isopropanol and water (40%:60%) and followed by a rinsing step with water.

The obtained scaffold was then fragmented by applying an extrusion force on the scaffold through a narrow tubular element.

B) Manufacture of an Implantable Soft Tissue Engineering Material Comprising a Multitude of Particles According to the Invention

Example 3

Carboxymethyl-cellulose (with a MW of 1500 kDa) was dissolved in deionized water to the concentration of 2,2%, and crosslinking initiated after precooling to 3° C. by means of addition of adipic acid dihydrazide AAD (0.08%) and a small excess of the carbodiimide EDC (0.5%) and buffered to a pH-value of 5.6 by means of an excess of MES buffer (54 mM). 20 mL of the reaction mixture was placed at −15° C. in a glass mold measuring 1 mm in depth and 16 cm diameter. After 20 hours, the scaffold was thawed and washed in 50 mL of DI water. The next step consisted in fracturing the scaffold. For this the bulk scaffold was stuffed into a 50 mL syringe and extruded through a 20 G needle by applying a pressure of 15 bars. The fractioned material obtained was further washed with 50 mL of a saline solution containing 0.45 g of NaCl. After the washing step, the material was autoclaved in a bottle of glass containing 90 mL of DI water using a temperature of 118° C. during 24 minutes. The content was then put onto a filter device with a pore size of 0.22 um and fluid withdrawn by briefly applying a suction pressure of 750 mbar such as to obtain a final volume of 10 mL The material was then transferred into a syringe with luer lock for injection.

Example 4

The fractioned material obtained in example 1 was further washed with phosphate buffered saline (PBS). The washing step was performed by thawing the fractioned material in a bath of saline solution. 10 mL of the fractioned material obtained in example 1 consisting of 0.6 g of dry polymer and of 9.4 g of water was washed with 50 mL of a saline solution containing 0.45 g of NaCl. After the washing step, the material was autoclaved in a bottle of glass containing 90 mL of DI water using a temperature of 121° C. during 20 minutes. The content of the bottle was then centrifuged using an acceleration of 4 g during 2 minutes; 50 mL of water was removed using a Becher and a pipette to obtain the final consistency. The consistency was adjusted by addition or withdrawal of fluid on a filter device; the final volume was about half of the original fabrication volume.

C) Comparative Tests

Example 5.1

Figure 6:
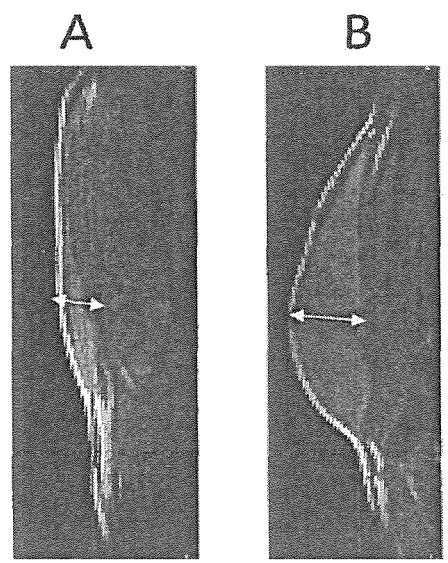
FIG. 6 shows 3-D projections of a material having a Young's modulus to low (A) and of a material according to the invention (B).

The Young's modulus of the soft tissue engineering material according to the invention, in conjunction with particle geometry and hydration level, enables the deployment of the branched sheets of the particles and consequently the 3D projection of the volume created (see FIG. 6). When the Young's modulus is too low, or the hydration too large, the material does not project in 3D but spreads (picture A of FIG. 6). When the Young's modulus and hydration level are correct, the material creates a 3D implant, stable over time (picture B of FIG. 6).

The effect of the mechanical properties of the soft tissue engineering material was further evaluated quantitatively by evaluation of the short-term (3 weeks) implantation behavior as a function of the mechanical properties of the implant. For this purpose, soft tissue engineering material fabricated according to 6 different recipes and characterized by their deployment pressure and Young's modulus of the soft tissue engineering material. The materials were injected subcutaneously in mice, and the implant evaluated with regard to undesired spreading from the injection site, evolution of volume for the first hour and then at three weeks, as well as regarding stability of shape and creation of a 3D projection. The results are summarized in table 1:

TABLE 1

| Recipe | Deployment pressure | Young's modulus (soft tissue engineering material) | In-vivo deployment | 3D projection | In-vivo shape maintenance |
|---|---|---|---|---|---|
| #1 | 4 Pa | 40 Pa | No | No | Flows |
| #2 | 19 Pa | 0.13 kPa | No | No | Flows |
| #3 | 32 Pa | 0.28 kPa | Inconsistent | Inconsistent | Inconsistent |
| #4 | 95 Pa | 0.74 kPa | Yes | Inconsistent | Inconsistent |
| #5 | 163 Pa | 1.5 kPa | Yes | Yes | Yes |
| #6 | 274 Pa | 3.3 kPa | Yes | Yes | Yes, but too hard to the touch |

They indicate for that for the implantation site and procedure chosen, a minimum of about 100 Pa of deployment pressure is needed to obtain a desired consistent (yet slight) volume swelling upon implantation, and that a Young's modulus of at least 1.5 kPa is required for stable 3D projection (not surprisingly, this approximately matches the known Young's modulus of 2 kPa for adipose tissue). Only slightly higher Young's moduli (3.3 kPa) are perceived as unnaturally hard to the touch from the outside. The Young moduli indicated are drained moduli; the undrained values are about 2.5× higher. The Poisson ratio under drained conditions was near zero, whereas it was near 0.5 for undrained conditions.

Uniaxial compression used for Young modulus determination was essentially perfectly reversible to high strains (at least 30%), both from geometric observation and return to baseline force within a few percent of the maximum force in particular for the drained conditions.

To further characterize the mechanics of the soft tissue engineering material, we analyzed samples obtained with recipe #5 of Table 1 in oscillatory rheology, and in uniaxial creep tests. For rheology, we used a HaakeRS100 RheoStress device, FL16 vane geometry with factory settings, stress sweep from 1 Pa to 100 Pa at constant 1 Hz frequency. At low stress (<10 Pa), the sample behaves like an elastic solid with minor viscous contribution (elastic modulus G' on the order of 5 kPa, viscous modulus G" about 0.9 kPa), whereas at higher stresses (20-30 Pa of shear stress in the FL16 vane geometry), a yield point is observed and the sample starts to flow with G' approaching G"; however, as soon as the movement is stopped, the samples recover their original G' and G" values at low frequency and stress (essentially perfect repeatability of the experiment without need for a setting period). This reversible, but nonlinear viscoelastic behavior contributes to injectability of the material (at shear stresses beyond yielding), and simultaneously its propensity to rapidly regain its stable solid-like properties once movement ceases.

Figure 7:
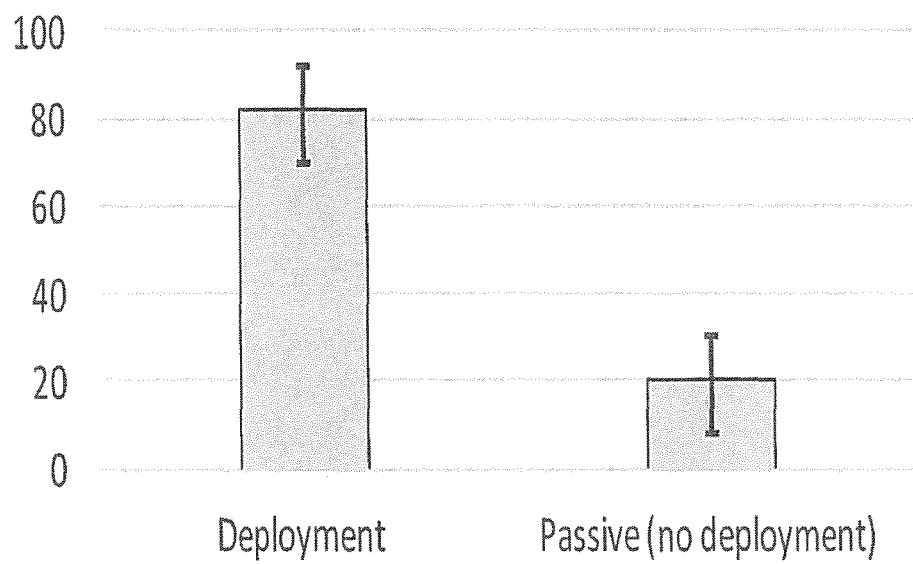
FIG. 7 is a graphical representation of the percentage of cells retained in the soft tissue engineering material according to the invention when seed in vitro with and without deployment effect.

Creep addresses how a material behaves under a constant load. We assessed creep during uniaxial compression (samples of an about 5 mm height under a chuck of 5 cm diameter), and found an uncommon behavior: For all pressures safely accessible to the uniaxial compression machine used (<2.5 kPa), chuck movement would completely stop at a finite sample height, indicating that for slow sample compression, the samples can withstand very substantial pressures equal to their Young modulus or higher. Local densification due to particle compressibility as well as efficient particle interlocking in the engineering material according to the invention are at the origin of this particular behavior. Surprisingly the effect is protective for the shape achieved in-vivo under slowly applied pressures (for instance, an individual lying down on an injected site). Deployment at low pressures enables the gentle aspiration of tissues or cell suspensions for co-grafting applications (mixing with adipose tissues and injection of the mixture to create a living volume). FIG. 7 shows the percentage of cells retained in the material obtained after seeding fibroblast cells using the deployment effect or using only a passive seeding (no deployment effect).

To achieve cell adhesion for the experiment described in relation to FIG. 7, material as prepared in example 3 was coated with collagen I (10% of the mass of CMC) in an sodium acetate buffer pH 4, followed DI rinsing and covalent attachment of the adsorbed collagen by use of EDC (10 mg/mL, in 100 mM MES buffer at pH 5.5), followed by inactivation of remaining EDC in basic pH and readjustment to physiological pH with PBS buffer. All steps made use of the deployment effect to enhance fluid exchange; the coating protocol is a result of optimization with respect to total collagen adsorption efficiency, homogeneity, collagen density lining the pores, absence of fibril formation and cell adhesion.

For measuring the effect of the deployment advantage of the particles according to the invention, two different materials were injected in mice:
  one which was partially hydrated, and once injected, deployment of the particles took place by taking up interstitial fluids; and
  another material the particles of which were fully hydrated, and once injected, would not deploy itself because the channel-like conduits were already "full" of fluid and therefore was not capable to deploy more.

Figure 8:
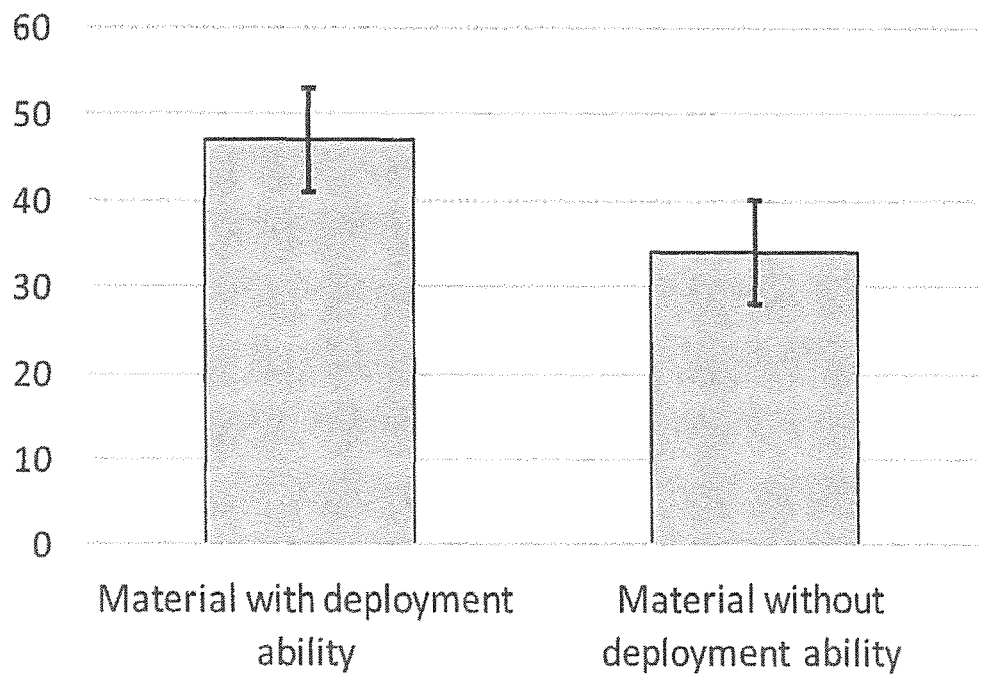
FIG. 8 is a graphical representation of the percentage of cellularization of the soft tissue engineering material according to the invention.

In both cases the percentage of the implant area occupied by cells and collagen or other proteins ("cellularization") was evaluated as shown in FIG. 8.

Further experiments were conducted with the two materials in order to confirm working hypothesis that the deployment of the partially hydrated particles by means of their peripheral protrusions was producing a zipper effect leading to stability of the shape of the injected material (implant) and of the volume created and preventing migration of the particles in the body.

The results obtained with the material with deployment ability clearly showed its superiority as represented in Table 2:

TABLE 2

| Material | Height of the implant measured after the injection (mm) | Standard deviation (mm) | Height of the implant 3 days after the injection (mm) | Standard deviation (mm) |
|---|---|---|---|---|
| With deployment ability | 3 | 1 | 3 | 1 |

TABLE 2-continued

| Material | Height of the implant measured after the injection (mm) | Standard deviation (mm) | Height of the implant 3 days after the injection (mm) | Standard deviation (mm) |
|---|---|---|---|---|
| Without deployment ability | 2 | 1 | 0.5 | 1 |

Surprisingly it seems that the material with deployment ability is frictioning with the surrounding tissues enabling the material to stay in place (anchoring effect).

Example 5.2

Since isotropicity of the conduits seems to play a major role in the deployment capability of the material further experiments were conducted in this regard. Indeed particles with high channel anisotropicity have long, highly oriented, parallel channels, and will collapse easily in the direction perpendicular to the channel orientation and therefore be unable to deploy correctly. In cross-sections of the particles, this anisotropy is visible by the occurrence of channels with very large ratios of longer to smaller diameter.

In order to verify these assumptions particles were manufactured with non-isotropic conduits and used for the manufacture of an implantable soft tissue engineering material comprising a multitude of such particles.

This material was compared to the material according to the invention by measuring the height of the implanted material immediately after the injection into the body and after 3 days. The results are shown in the below table. It was observed that the 3D deployment was reduced in the non-isotropic like conduits as shown in table 3:

TABLE 3

| Material | Height of the implant measured after the injection (mm) | Standard deviation (mm) | Height of the implant measured 3 days after the injection (mm) | Standard deviation (mm) |
|---|---|---|---|---|
| With isotropic conduits | 4 | 1 | 3 | 1 |
| With non-isotropic conduits | 2 | 1 | 0.5 | 1 |

D) Role of the Mean Diameter of the Conduits on the Vessels Ingrowth

Figure 12:
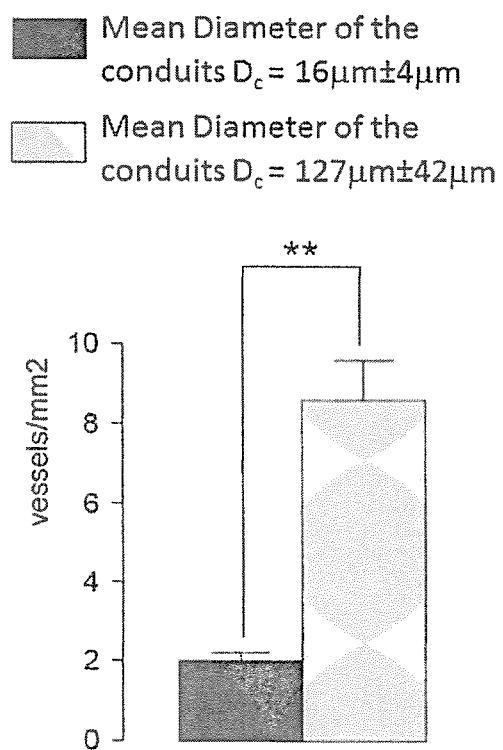
FIG. 12 is a graph showing the vessels density (number of vessels/mm$^2$) observed on histology pictures after the implantation of a soft tissue engineering material having a mean diameter of the conduits of 16 micrometers and a soft tissue engineering material having a mean diameter of the conduits of 127 micrometers.

Since mean diameter of the conduits plays a major role in the vascularization of the material once implanted in vivo, further experiments were conducted in this regard. The graph in FIG. 12 shows the vessels density (number of vessels/mm2) observed on histology pictures after the implantation of a soft tissue engineering material having a mean diameter of the conduits of 16 micrometers and a soft tissue engineering material having a mean diameter of the conduits of 127 micrometers. We observe that the vessels density is significantly lower in the case of the smallest mean diameter of the conduits.

E) Clinical Use of the Implantable Soft Tissue Engineering Material According to the Invention Example 6.1

Prior the intervention, the surgeon using the soft tissue engineering material defines the areas where new volumes are needed. For this, he/she evaluates visually the volume defects and traces lines using a marker defining the future injection lines.

10 mL of the soft tissue engineering material was placed in a plastic syringe equipped with a Luer-lock connector tip (corresponding to 0.6 g of dry mass of polymer). A cannula was connected to the tip and inserted in the target area of the patient through a thin skin incision. Once positioned in the target site, for example between the subcutaneous adipose layer and the pectoral muscle in a woman breast, the cannula is withdrawn at a speed of 0.5 cm/s while 10 mL of the material is injected by the surgeon by applying a pressure on the piston of the syringe of 4000 N/m$^2$. The injection can be repeated in a neighboring area, enabling to increase the total volume injected.

Example 6.2

The injection of 10 mL of the soft tissue engineering material is repeated by using the same incision point as in example 6.1. but by modifying the direction and the angle of the cannula between each injection.

The surgeon performed one incision through the skin of the patient close to the area needing volume enhancement. The Luer-lock syringe containing the soft tissue engineering material was screed to a cannula (14 G for example) and the cannula was inserted in the patient's tissues. The cannula was inserted into the tissues up to reaching the target and the injection of 10 mL of the soft tissue engineering material was started by applying a pressure of 4 kPa to the piston of the syringe while withdrawing the cannula in the direction of the incision point. Then, without taking the cannula out of the patient's body, the empty syringe was unscrewed and a new filled syringe containing the soft tissue engineering material was screwed on and a new injection was performed in a new direction of interest, predefined by marked lines on the patient's skin.

Example 6.3

In another embodiment, the soft tissue reconstruction material is first mixed with adipose tissues from the patient using two syringes and a connector before being injected as a mixture into the target area using a cannula.

Example 6.4

In one embodiment, the soft tissue engineering material is combined with the graft of adipose tissues preliminary harvested from the patient. For example, adipose tissues are extracted by liposuction using a harvesting cannula connected to a 10 mL Luer-lock syringe. Tissues are let sediment for 5 minutes allowing to remove the blood and oil floating above the adipose tissues. In one embodiment, the user injects one spaghetti of adipose tissues of 2 mL to 10 mL and then he/she injects a spaghetti of the soft tissue engineering material. In another embodiment, the adipose tissues are mixed with the soft tissue engineering material by connecting two syringes (one containing the adipose tissues, the other one containing the soft tissue engineering material) using a Luer-to Luer connector and by pushing sequentially on the two pistons of the two syringes until obtaining a homogeneous mixture. The mixture obtained is then injected using the injection method described before.

Example 6.5

In another embodiment, the material is injected in the target area and the shape of the implant is shaped manually by the surgeon from the outside of the patient in order to create the shape required.

Example 6.6

In one embodiment, the implantable soft tissue engineering material is sterile and contained in a syringe. It is delivered in the target area of the patient using a tubular element such as a sterile Luer-lock infiltration Coleman cannula of 14 Gauge. Typically, the material is injected into subcutaneous tissues, into adipose tissues, into muscular tissues, between two layers of the above-mentioned tissues. For the delivery, the user performs first a small incision (1 mm to 4 mm in length) located at least at 2 cm of the targeted injection site. The user inserts the cannula through the incision up to reaching the targeted point, located at 2 cm to 15 cm from the insertion point. He/she then injects retro-gradually 5 mL of the soft tissue engineering material by pushing gradually on the piston of the syringe while withdrawing the cannula from the targeted point to the incision point. So doing, the user injects a spaghetti like volume having a diameter comprised between 1 mm and 8 mm, enabling the integration of the soft tissue engineering material within the surrounding tissues. The procedure can be repeated several times from the same injection point in order to create a 3D arrangement of spaghettis. The localization of the spaghettis is controlled manually by the user, who is able to evaluate the depth of the injection and the localization in the different planes of the patient's tissues.

Other Variations of Examples 6.1. to 6.6. are Described Below

In one embodiment, the user uses his/her hands to press on the skin of the patient while inserting the cannula and injecting the material in order to maintain the patient's tissues from the outside and to define the localization of the material.

In one embodiment, the user injects the material using the same device described previously but injects the material in a bolus shape, which is expanding the surrounding tissues of the injection site.

In one embodiment, the soft tissue engineering material is combined with the graft of adipose tissues preliminary harvested from the patient. For example, adipose tissues are extracted using a harvesting cannula by liposuction. Tissues are let sediment for 5 minutes allowing to remove the blood and oil floating above the adipose tissues. The adipose tissues are distributed in 10 mL syringes. In one embodiment, the user injects one spaghetti of adipose tissues of 2 mL to 10 mL using the Coleman method and then he/she injects a spaghetti of the soft tissue engineering material. In another embodiment, the adipose tissues are mixed with the soft tissue engineering material by connecting two syringes (one containing the adipose tissues, the other one containing the soft tissue engineering material) using a Luer-to-Luer connector and by pushing sequentially on the two pistons of the two syringes. The mixture obtained is then injected using the method described before.

In another embodiment, the soft tissue engineering material is manually distributed in a body cavity (such as a breast cavity after silicone implant removal) using a sterile spatula in order to create a layer of the soft tissue engineering material.

In another embodiment, the soft tissue engineering material is sutured to surrounding tissues (in the case of large particles).

F) Clinical Results Obtained and Comparative Studies with Prior Art Materials

Example 7

A comparison of the stability and migration of 4 different materials, including the soft tissue engineering material according to the invention was performed. The materials were the following:

"HA 1" is a commercially available hyaluronic acid based filler ("Juvederm Ultra 2" from Allergan.

"HA 2" is a commercially available, strongly crosslinked hyaluronic acid based filler ("Macrolane" from Q-med AB).

"Matrix" is a commercially available, collagen based, flowable matrix used for wound repair (from Integra LifeSciences corporation).

"Material developed" is the material obtained in examples 1 to 4.

Figure 9:
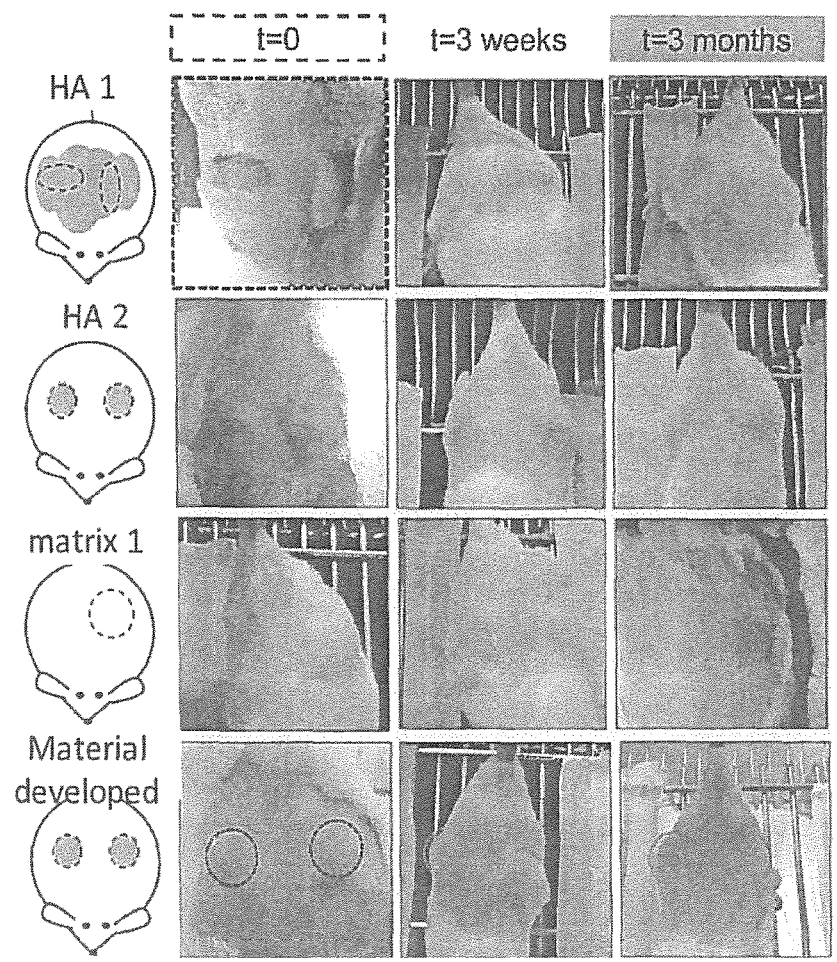
FIG. 9 shows macroscopic pictures of the implants site over time.

A defined volume of the different tested items (200 microliters) was injected subcutaneously in CD1 female mice in the back area of the animal. Two samples of each tested item were injected, namely one on each side of the spinal cord of the animal. In the case of the silicone item, the samples were implanted by first performing an incision in the skin of the animal and by inserting manually with tweezers the layer of silicone. The volumes of the items were monitored over time using external measurements with a Caliper and using MRI scanning and MRI images analysis. After 3 and 6 months, the animals were euthanized and histology of the different implanted materials was performed. Bio-integration (percentage of the material occupied by cells and tissues, vascularization) was quantified. The results are represented in FIG. 9, which shows macroscopic pictures of the implants site in mice for the different tested items, at different time points (t=0 is just after the injection step). In the drawings on the left side of FIG. 9, the dashed lines represent the implant localization just after the injection. The grey surface represents the implant localization 3 months after the injection.

Figure 10:
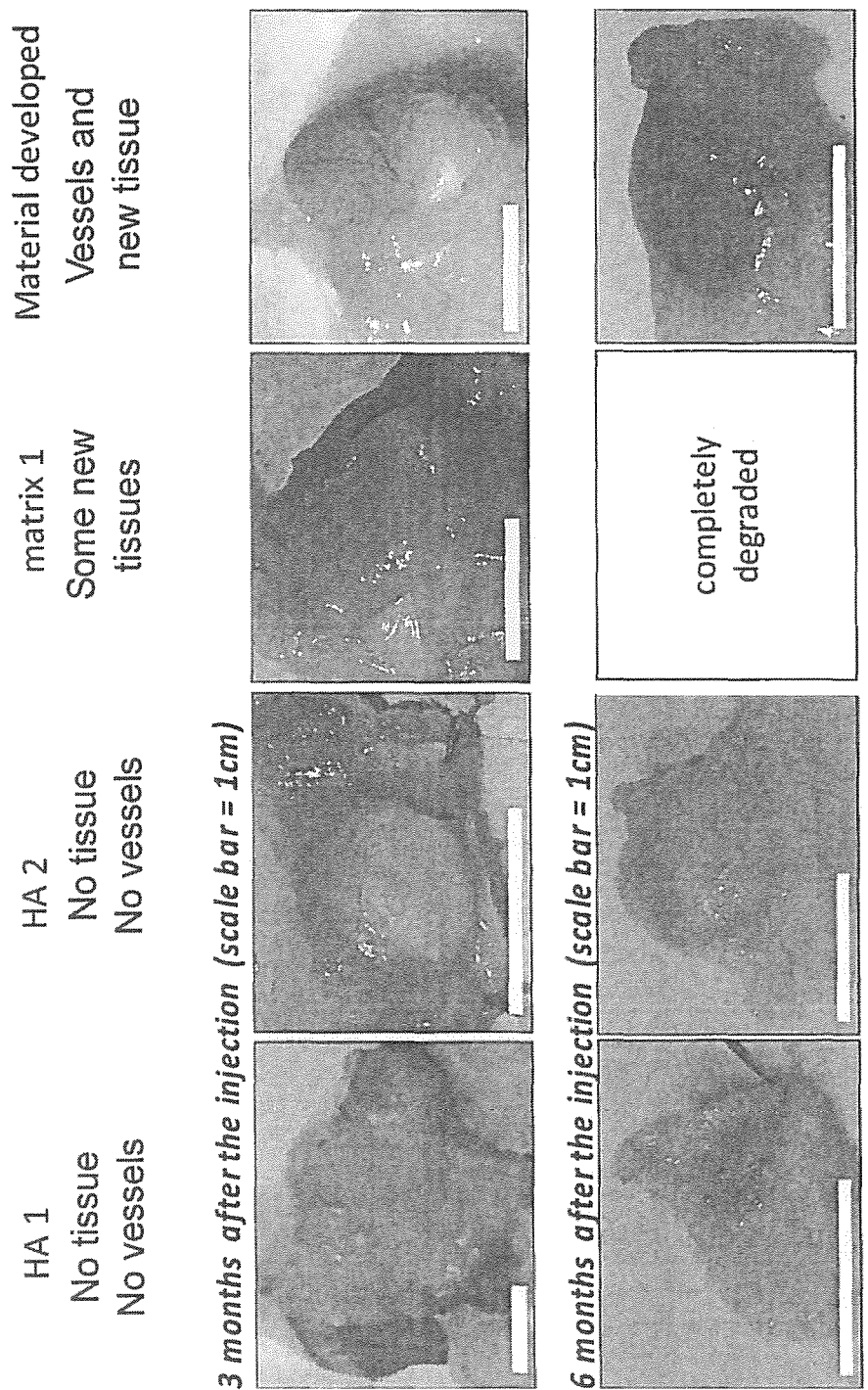
FIG. 10 represents photographs regarding histology and macroscopic observation of bio-integration of comparative examples.
Figure 11:
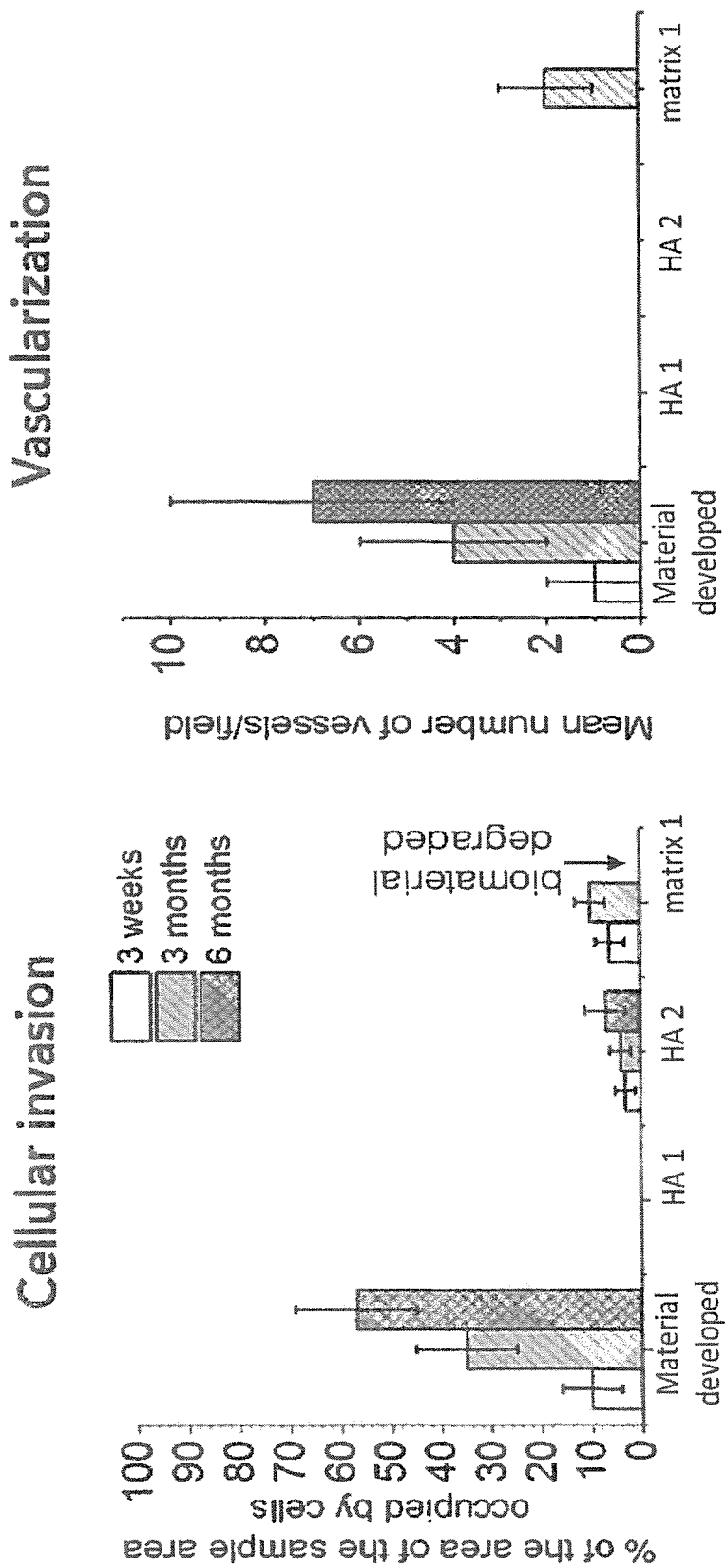
FIG. 11 is a graph showing cellular invasion and vascularization of comparative examples.

The macroscopic observation of the histology samples (see FIG. 10) enabled to show that the material developed lead to the growth of vessels and tissues, whereas the HA-based materials tested remained clear and transparent, showing neither tissular nor vascular ingrowth. The Matrix 1 material was populated with cells but it degraded before the 6 months timepoint. These results are represented graphically in FIG. 11.

The presence of a capsule surrounding the implants compared was investigated on histological sections stained with Masson trichrome. An additional material was included in this comparative study, namely "Silicone" which a silicone layer sample cut from a silicone tissue expander used in breast (Natrelle 133) Tissue expander from Allergan. The implanted samples were squares of 6 mm side and measured 1.5 mm in thickness.

The thickness of the capsule was measured for each material tested. The results are presented in Table 4 below:

TABLE 4

| Material implanted | Material developed | HA1 | HA2 | Matrix 1 | Silicone |
|---|---|---|---|---|---|
| Thickness of the capsule (3 months after the implantation) | No capsule | No capsule | 92 +/− 17 micrometers | No capsule | 104 +/− 20 micrometers |

It was observed that the soft tissue engineering material according to the invention was stable over time. It did not migrate or increase in volume. On the contrary, HA 1 was increasing in volume and the two implants merged together (they moved from the initial position). HA 2 was also stable but the histological analysis showed the presence of a foreign body reaction (thin capsule around the implant, presence of giant cells), which could explain the stability of the position. The material was isolated from the body and did not migrate. The matrix 1 material was rapidly resorbed and did not produce a durable volume.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A particle for use in manufacturing an implantable soft tissue engineering material, the particle comprising a three-dimensionally warped and branched sheet, wherein:
   (i) the three-dimensionally warped and branched sheet comprises a biocompatible material having a Young's modulus of 1 kPa to 1 GPa;
   (ii) the three-dimensionally warped and branched sheet has an irregular shape which is encompassed in a virtual three-dimensional envelope having a volume $V_E$;
   (iii) the three-dimensionally warped and branched sheet has a mean sheet thickness T;
   (iv) the three-dimensionally warped and branched sheet has a volume $V_S$;
   (v) the particle has a Young's modulus of 100 Pa to 15 kPa; and
   (vi) the particle has an irregular shape and comprises a number of protrusions where the three-dimensionally warped and branched sheet reaches the virtual three-dimensional envelope;
   (vii) the particle has a number of interconnected channel-type conduits defined by the branching of the sheet and/or by voids in the sheet; and
   (viii) the conduits have
      (a) a mean diameter $D_C$; and
      (b) an anisotropicity index of 1.01 to 5.00, and
   (ix) wherein the ratio of $D_C/T$ is larger than 1.

2. The particle according to claim 1, wherein the biocompatible material of the sheet is selected from the group consisting of poly-ethyleneglycol (PEG), poly-acrylamide, poly-(hydroxyethyl)methacrylate, and polysaccharides.

3. The particle according to claim 1, wherein the biocompatible material of the sheet is a material selected from the group consisting of carbohydrates, collagens, peptides, and extracellular matrices.

4. The particle according to claim 1, wherein the biocompatible material of the sheet is a synthetic polymer selected from the group consisting of
   (i) silicones;
   (ii) polyurethanes;
   (iii) polyolefins;
   (iv) acrylates; and
   (v) polyamides.

5. The particle according to claim 1, wherein the mean diameter $D_C$ of the conduits is larger than 1 micrometer.

6. The particle according to claim 1, wherein the protrusions have a mean relative maximum protrusion depth in the range between 0.05 and 1.0.

7. The particle according to claim 1, wherein the shape of the three-dimensionally warped and branched sheet is flexible and reversibly expandable upon absorption or removal of a liquid by the biocompatible material.

8. The particle according to claim 1, wherein the contact angle between water and the biocompatible material of the sheet is in the range of 0° to 90°.

9. The particle according to claim 1, wherein the sheet is reversibly compressible.

10. The particle according to claim 1, wherein the particle is hydrated and comprises at least 0.05 weight-% of the biocompatible material based on the total weight of the hydrated particle.

11. The particle according to claim 1, wherein the particle comprises a plurality of three-dimensionally warped and branched sheets.

12. A composition comprising:
   a) a multitude of particles according to claim 1; and
   b) a physiologically acceptable fluid.

13. The composition according to claim 12, wherein the amount of fluid is such that the particles are only partially hydrated.

14. An implantable soft tissue engineering material comprising a multitude of particles according to claim 1.

15. The implantable soft tissue engineering material according to claim 14, wherein the multitude of particles is admixed with one or more substances to form a malleable paste, and wherein the one or more substances are selected from the group consisting of: water, aqueous solution, blood, serum, pharmaceutically active agents, lidocaine, adrenaline, cell suspensions, biological tissues, stem cells, virus, bacteria, fungi, transfecting agents, antibodies, genetically modified cells, extracellular matrices, co-cultures of cells, growth factors, platelet rich plasma, cell differentiation factors, lipids, and high-density lipoprotein (HDL).

16. The implantable soft tissue engineering material according to claim 14, wherein the implantable soft tissue engineering material is reversibly compressible after injection into a patient by uptaking liquid from surrounding tissues.

17. A method for manufacturing particles according to claim 1, comprising:
   a) pre-cooling a mixture comprising a polymerizable biocompatible material in an aqueous solution at a temperature below 10° C.;
   b) cross-linking the pre-cooled mixture at a temperature below 0° C. such that the cross-linking is not based on a radical polymerization; and
   c) fractioning the cross-linked biocompatible material obtained.

18. The method according to claim 17, wherein adipic dihydrazide is used as a cross-linker.

19. The particle according to claim 1, wherein the biocompatible material of the sheet is a hydrogel.

20. The particle according to claim 1, wherein the biocompatible material of the sheet is selected from the group consisting of cellulose, alginate, chitosan, agarose, polysucrose, and dextran.

21. The particle according to claim 1, wherein in use, when a neighboring second particle is present, the two particles interlock.

* * * * *